United States Patent
Lin et al.

(10) Patent No.: US 9,144,418 B2
(45) Date of Patent: Sep. 29, 2015

(54) APPARATUS, SYSTEM, AND METHOD FOR ADAPTIVELY CONTROLLING A FRAME INTERVAL BETWEEN ULTRASOUND SCANNING FRAMES FOR AN ULTRASOUND ELASTICITY IMAGING SCAN

(75) Inventors: Feng Lin, Niskayuna, NY (US); Christopher Robert Hazard, Niskayuna, NY (US); Mirsaid Seyed-Bolorforosh, Albany, NY (US); Karsten Hiltawsky, Schwerte (DE); Zhe Wu, Waukesha, WI (US)

(73) Assignee: General Electric Company, Schenectady, NY (US)

(*) Notice: Subject to any disclaimer, the term of this patent is extended or adjusted under 35 U.S.C. 154(b) by 753 days.

(21) Appl. No.: 13/399,361

(22) Filed: Feb. 17, 2012

(65) Prior Publication Data

US 2012/0150040 A1    Jun. 14, 2012

Related U.S. Application Data

(62) Division of application No. 11/567,285, filed on Dec. 6, 2006, now Pat. No. 8,123,692.

(51) Int. Cl.
*A61B 8/08* (2006.01)
*G01N 29/04* (2006.01)
*G01S 7/52* (2006.01)

(52) U.S. Cl.
CPC .............. *A61B 8/485* (2013.01); *G01N 29/041* (2013.01); *G01N 29/043* (2013.01); *G01S 7/52085* (2013.01); *A61B 8/08* (2013.01); *A61B 8/0858* (2013.01)

(58) Field of Classification Search
CPC .... A61B 8/0858; A61B 8/0891; A61B 8/485; G01N 29/041; G01N 29/043
See application file for complete search history.

(56) References Cited

U.S. PATENT DOCUMENTS

| 4,888,694 | A | * | 12/1989 | Chesarek | 600/454 |
|---|---|---|---|---|---|
| 5,289,820 | A | | 3/1994 | Beach et al. | |
| 5,501,223 | A | * | 3/1996 | Washburn et al. | 600/455 |
| 5,919,139 | A | | 7/1999 | Lin | |
| 6,558,324 | B1 | | 5/2003 | Von Behren et al. | |
| 6,913,574 | B2 | | 7/2005 | Jeong et al. | |
| 2005/0101863 | A1 | | 5/2005 | Kawagishi et al. | |
| 2006/0025682 | A1 | | 2/2006 | Vanderby et al. | |
| 2006/0173306 | A1 | * | 8/2006 | Matsumura et al. | 600/437 |
| 2006/0173320 | A1 | | 8/2006 | Radulescu | |
| 2008/0188743 | A1 | * | 8/2008 | Waki et al. | 600/438 |

* cited by examiner

*Primary Examiner* — Tse Chen
*Assistant Examiner* — Nate S Sunwoo
(74) *Attorney, Agent, or Firm* — The Small Patent Law Group LLC; Christopher R. Carroll

(57) ABSTRACT

An apparatus, system and method for adaptively controlling a frame interval between ultrasound scanning frames of an ultrasound elasticity imaging scan. The system includes a transmitter for transmitting ultrasound beams to a subject during an ultrasound elasticity imaging scan, and a receiver for receiving ultrasound beam echoes from the subject responsive to transmitted ultrasound beams. The system also includes a processor for processing a plurality of the ultrasound beam echoes to determine a strain variation of the tissue undergoing strain, calculating a value for an ultrasound scanning frame interval adapted for imaging the tissue undergoing the determined strain variation, and setting the value of the ultrasound scanning frame interval for acquiring ultrasound elasticity images of the tissue undergoing the determined strain variation.

15 Claims, 4 Drawing Sheets

APPARATUS, SYSTEM, AND METHOD FOR ADAPTIVELY CONTROLLING A FRAME INTERVAL BETWEEN ULTRASOUND SCANNING FRAMES FOR AN ULTRASOUND ELASTICITY IMAGING SCAN

CROSS REFERENCE TO RELATED APPLICATIONS

The present application claims priority to U.S. patent application Ser. No. 11/567,285, filed Dec. 6, 2006, and entitled "APPARATUS, SYSTEM, AND METHOD FOR ADAPTIVELY CONTROLLING A FRAME INTERVAL BETWEEN ULTRASOUND SCANNING FRAMES FOR AN ULTRASOUND ELASTICITY IMAGING SCAN", the entirety of which is incorporated by reference.

BACKGROUND

Embodiments of the present invention are generally related to imaging systems, and, more particularly, to adaptively controlling a frame interval between ultrasound scanning frames for an ultrasound elasticity imaging scan.

Ultrasound elasticity imaging is useful for distinguishing tissues having different elastic properties. To perform ultrasound elasticity imaging of tissue in a desired region of interest (ROI), the tissue is excited, or palpated, by an external force, such as by manual palpitation, vibrational devices, and/or ultrasound beams. Alternatively, tissue may be excited by internal forces, such as forces resulting from a heart beat or blood vessel pulsation. Tissue deformation responsive to the excitation may be detected by directing ultrasound beams at the excited tissue and monitoring ultrasonic pulse echoes from the tissue at different times during excitation to obtain strain information related to elasticity of the tissue. Because strain is a function of a derivative of displacement, at least two time separated imaging frames received from the deformed tissue are required for each estimate of strain. Accordingly, elasticity imaging relies on sensing tissue deformation between two imaging frames to obtain strain information.

In conventional ultrasound elasticity imaging, a time interval between imaging frames to be compared for obtaining strain information is typically fixed a constant value. The fixed time interval is typically selected based on a general knowledge about the strain force being applied, such as a frequency and/or amplitude of the force. However, there may be times during elasticity imaging when there is no displacement, or only rigid displacement between frame intervals. Consequently, strain information may be difficult, if not impossible, to obtain. Conversely, when a deformation during a frame interval is too great, the resulting echoes may be insufficiently correlated to enable a reliable strain estimation.

BRIEF DESCRIPTION

In an example embodiment, the invention includes a method for adaptively controlling a frame interval between ultrasound scanning frames of an ultrasound elasticity imaging scan, each frame including a plurality of ultrasound beams. The method includes acquiring a plurality of ultrasound beam echoes from tissue undergoing strain and processing the acquired plurality of ultrasound beam echoes to determine a strain variation of the tissue undergoing strain. The method also includes calculating a value for an ultrasound scanning frame interval adapted for imaging the tissue undergoing the determined strain variation and setting the value of the ultrasound scanning frame interval for acquiring ultrasound elasticity images of the tissue undergoing the determined strain variation.

In another example embodiment, the invention includes a method for adaptively controlling a frame interval between ultrasound scanning frames for an ultrasound elasticity imaging scan. The method includes positioning a source of ultrasound beams proximate a subject for performing an ultrasound elasticity imaging scan of tissue of the subject undergoing strain and acquiring a plurality of ultrasound beam echoes from the tissue. The method includes processing the acquired plurality of ultrasound beam echoes to determine a strain variation of the tissue undergoing strain based on a distance of the tissue from the source. The method also includes calculating a value for an ultrasound scanning frame interval adapted for imaging the tissue undergoing the determined strain variation and setting the value of the ultrasound scanning frame interval for acquiring ultrasound elasticity images of the tissue undergoing the determined strain variation.

In another example embodiment, the invention includes an apparatus for adaptively controlling a frame interval between ultrasound scanning frames of an ultrasound elasticity imaging scan. The apparatus includes a first module for acquiring a plurality of ultrasound beam echoes from tissue undergoing strain and a second module for processing the acquired plurality of ultrasound beam echoes to determine a strain variation of the tissue undergoing strain. The invention also includes a third module for calculating a value for an ultrasound scanning frame interval adapted for imaging the tissue undergoing the determined strain variation and a fourth module for setting the value of the ultrasound scanning frame interval for acquiring ultrasound elasticity images of the tissue undergoing the determined strain variation.

In another example embodiment, the invention includes a system for adaptively controlling a frame interval between ultrasound scanning frames of an ultrasound elasticity imaging scan. The system includes a transmitter for transmitting ultrasound beams to a subject during an ultrasound elasticity imaging scan and a receiver for receiving ultrasound beam echoes from the subject responsive to transmitted ultrasound beams. The invention also includes a processor for processing a plurality of the ultrasound beam echoes to determine a strain variation of the tissue undergoing strain, calculating a value for an ultrasound scanning frame interval adapted for imaging the tissue undergoing the determined strain variation, and setting the value of the ultrasound scanning frame interval for acquiring ultrasound elasticity images of the tissue undergoing the determined strain variation.

In another example embodiment, the invention includes computer readable media containing program instructions for adaptively controlling a frame interval between ultrasound scanning frames of an ultrasound elasticity imaging scan. The computer readable media includes a computer program code for acquiring a plurality of ultrasound beam echoes from tissue undergoing strain and a computer program code for processing the acquired plurality of ultrasound beam echoes to determine a strain variation of the tissue undergoing strain. The computer readable media also includes a computer program code for calculating a value for an ultrasound scanning frame interval adapted for imaging the tissue undergoing the determined strain variation and a computer program code for setting the value of the ultrasound scanning frame interval for acquiring ultrasound elasticity images of the tissue undergoing the determined strain variation.

DETAILED DESCRIPTION

Figure 1:
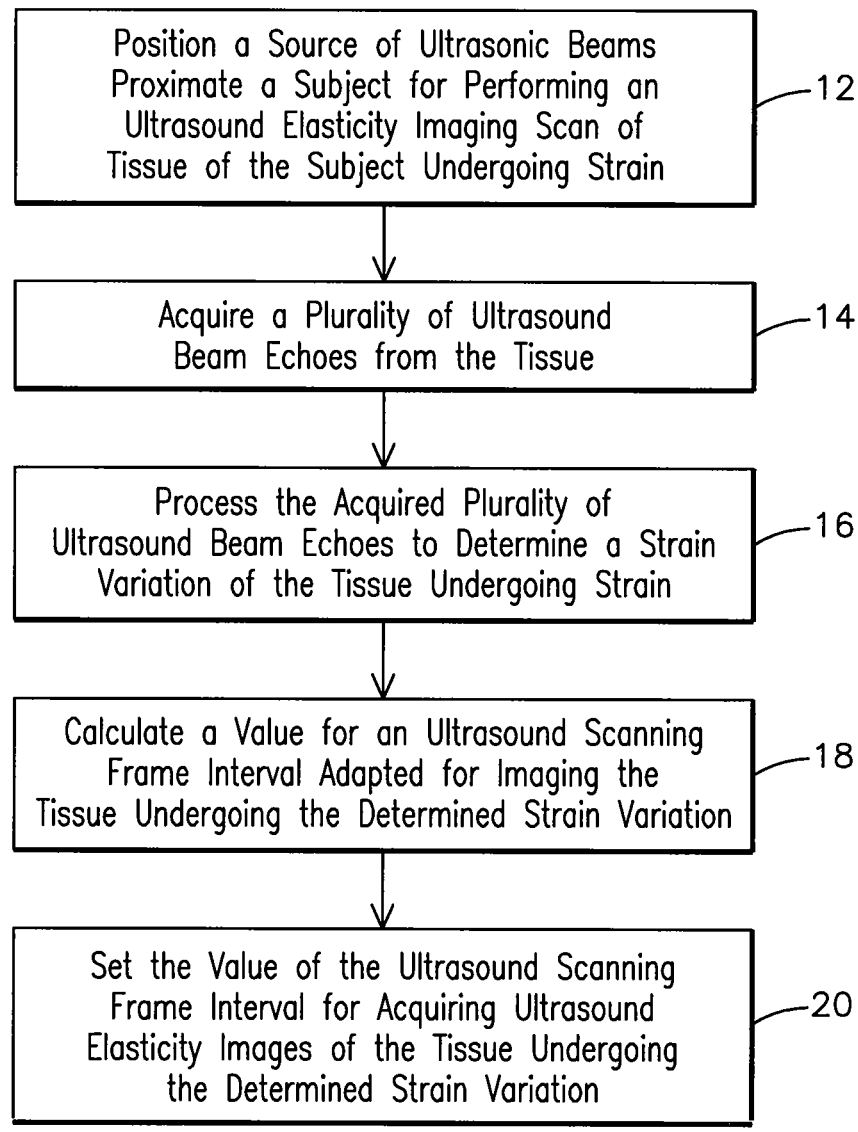
FIG. 1 shows a block diagram of an example method for adaptively controlling a frame interval between ultrasound scanning frames for an ultrasound elasticity imaging scan.

The inventors have recognized that improved elasticity imaging may be achieved by adaptively adjusting an ultrasound elasticity imaging frame interval responsive to a strain variation of tissue being imaged. FIG. 1 shows a block diagram 10 of an example method for adaptively controlling a frame interval between ultrasound scanning frames for an ultrasound elasticity imaging scan. The method may include positioning a source of ultrasonic beams proximate a subject for performing an ultrasound elasticity imaging scan of tissue of the subject undergoing strain 12. The method may then include acquiring a plurality of ultrasound beam echoes from tissue undergoing strain 14, for example, for at least two ultrasound scan frames.

Figure 2:
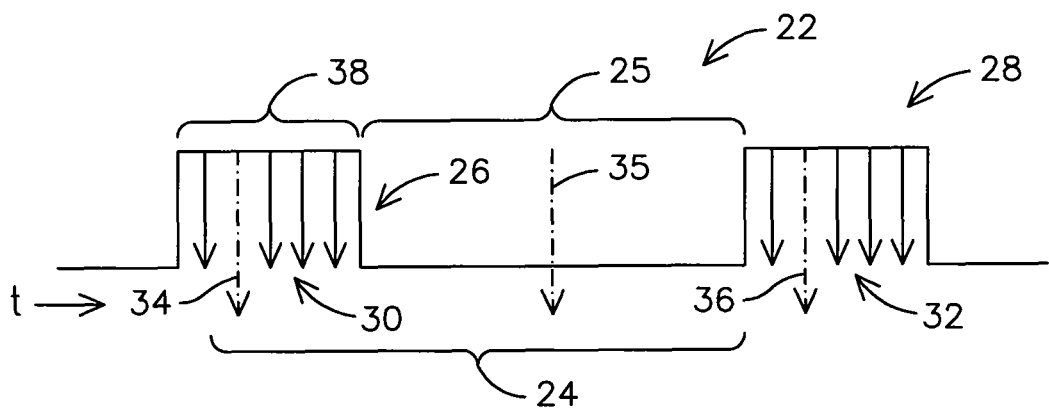
FIG. 2 is a schematic timing diagram showing an example frame interval between two ultrasound scan frames.

FIG. 2 is schematic timing diagram 22 showing an example frame interval 24 between two ultrasound scan frames 26, 28 having a frame length 38 useful for explaining certain aspects of the invention. Each ultrasound scan frame 26, 28 may include a number of ultrasound scanning beams 30, 32 fired during the frame 26, 28 according to a desired scan sequence. In an embodiment, a reduced number of ultrasound beams than normally used for ultrasound scanning, i.e., detective beams 34, 35, 36, may be used during a strain variation determination process, for example, independently of beam scan frames used for normal imaging. The detective beams 34, 35, 36 may be equally spaced in time and may have a different pulse repetition interval (PRI) than a PRI that is used for normal scan frames, such as scan frames 26, 28. The detective beams 34, 35, 36 may be interleaved inside a frame, or may be used in an inter-frame region 25. In an embodiment, the detective beams 34, 35, 36 may be asynchronous with respect to normal scan frames.

Returning to FIG. 1, the ultrasound echo beams acquired in step 14 may be responsive to detective beams, such as detective beams 34, 35, 36, directed at the tissue undergoing strain. The detective beams, such as detective beams 34, 35, 36, may be fixed at predetermined positions within a ROI of a subject. In one example embodiment, the detective beams may be configured to be equally distributed in a ROI. In another embodiment, a time interval between the detective beams 34, 35, 36 may be predetermined. By limiting a number of beams used to acquire the ultrasound beam echoes in step 14, a processing requirement and a corresponding processing time may be reduced compared to having to process all beams of a normal scan frame.

After the beam echoes, for example, from at least the detective beams, are acquired for at least two frames, the method may include processing the acquired plurality of ultrasound beam echoes to determine a strain variation of the tissue undergoing strain 16. In one example embodiment, an average strain between frames may be determined for use as an estimate for strain variation. Average strain may be calculated as a function of tissue depth using known techniques, such as direct strain estimation, and then averaging the strain along the depth. In another example embodiment, displacements at certain depths may be estimated using, for example, a known cross correlation method. The corresponding strains may then be calculated by dividing the displacements by the corresponding depths and averaging the resulting strains.

After a strain variation has been determined, the method may include calculating a value for an ultrasound scanning frame interval that is adapted for imaging the tissue undergoing the determined strain variation 18. In an aspect of the invention, calculating this value may be performed based on at least one of the determined strain variation, the predetermined time interval of detective beams, and a desired amount of strain, such as an optimal amount of strain. An optimized ultrasound scanning frame interval value may correspond to acquiring beam echoes at time intervals when strain has a desired profile, such as desired average strain.

A strategy for calculating a value of a frame interval may be different depending on how an external force is applied during elasticity scanning. For example, when using free hand palpation, the strain variation may be comparatively slow, so that a desired value of a frame interval may be derived directly from an average determined strain variation. Accordingly, a frame interval may be calculated according equation 1:

$$T = \frac{St}{s} \qquad 1)$$

where s represents the average strain, t represents a predetermined time interval of detective beams, S represents a strain variation corresponding to a preferred strain profile, and T represents the desired ultrasound scanning frame interval.

When a vibrational device is used to impart an external force, the resulting strain variation is typically periodic. Accordingly, a history of the average strain may be used to estimate a period and a phase of the variation. A desired ultrasound scanning frame interval may be selected to synchronize beam echo acquisition with the periodic strain variation.

Once a value for a frame interval has been calculated, the method may include setting the value of the ultrasound scanning frame interval for acquiring ultrasound elasticity images of the tissue undergoing the determined strain variation 20. In an aspect of the invention, steps 14-20 may be sequentially repeated while imaging the tissue undergoing strain so that the frame interval is dynamically adapted, for example, in real time, or near real time, to ensure that beam echoes are acquired at a frame interval that is desired for improved elasticity imaging compared to a fixed frame interval.

Figure 3:
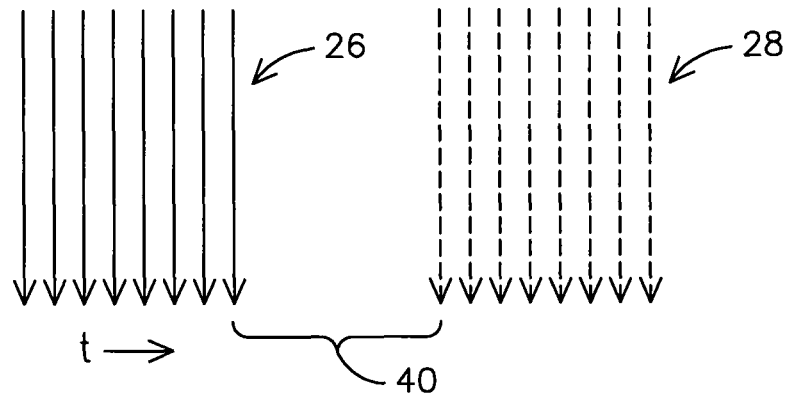
FIG. 3 shows an example scanning sequence for an ultrasound elasticity scan according to an embodiment of the invention.

In an aspect of the invention, the determined strain variation may affect the frame length and/or a scanning sequence used within the frame to acquire elasticity images. A nominal frame length may be determined by a number of beams in a tissue ROI and an allowable minimum time interval between ultrasound beams. The minimum time interval between ultrasound beams may be limited by a distance between a source of ultrasound beams from the tissue ROI and an acoustic attenuation of the tissue. For example, as shown in FIG. 3, with reference to FIG. 2, when a value of a frame interval 24 is greater than a frame length 38 of an ultrasound scanning frame, a blank interval 40 may be inserted between the ultrasound scan frames 26, 28.

Figure 4:
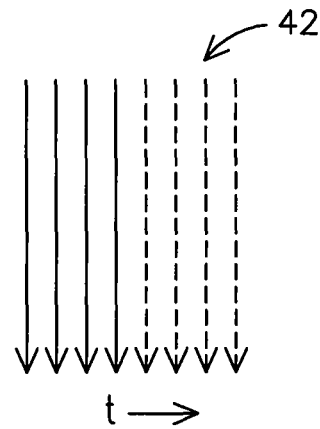
FIG. 4 shows an example scanning sequence for an ultrasound elasticity scan according to another embodiment of the invention.

However, when a value of the ultrasound scanning frame interval 24 needs to be less than a length 38 of an ultrasound scanning frame, scanning sequences of the beams 30, 32 may need to be modified to accommodate a frame interval 24 less than a frame length 38. For example, a number of beams in a frame may be reduced to fit within a frame length 38 less than or equal to a frame interval 24. Reducing a number of beams to fit within a frame interval 24 may include truncating at least one of the beams in at least one of two frames and then concatenating the remaining beams of the two frames so that at least some beams of each of the two frames are scanned during the frame interval 24. As shown in FIG. 4, beams 30 from one frame (indicated by continuous lined arrows) and beams from another frame 32 (indicated by dashed lined arrows) are concatenated in a single frame 42.

Figure 5:
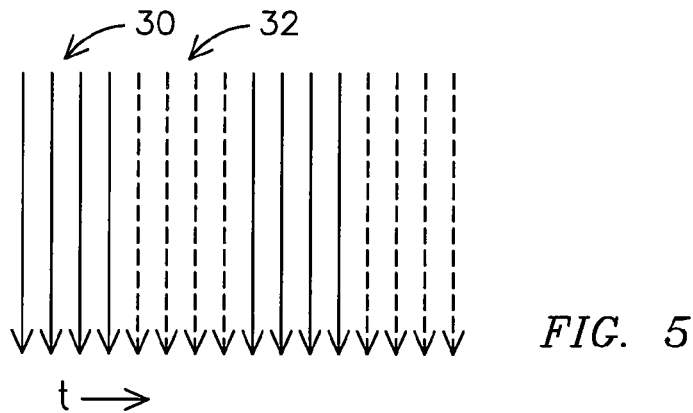
FIG. 5 shows an example scanning sequence for an ultrasound elasticity scan according to another embodiment of the invention.

In another example embodiment, interleaving of beams may be used to ensure that beams from different frames fit within a frame length 38 less than or equal to a frame interval 24, such as by interleaving beams of a first frame with beams of a second frame so that at least some beams of each of the first and second frames are scanned during a frame interval 24. Interleaving may include grouping beams from each of the frames into respective beam groups and then interspersing the beam groups of the first frame between beam groups of the second frame. As shown in FIG. 5, a group of beams 30 from one frame (indicated by continuous lined arrows) and a group of beams 32 from another frame (indicated by dashed lined arrows) are interleaved so beams from both frames are scanned during a frame interval 24.

Figure 6:
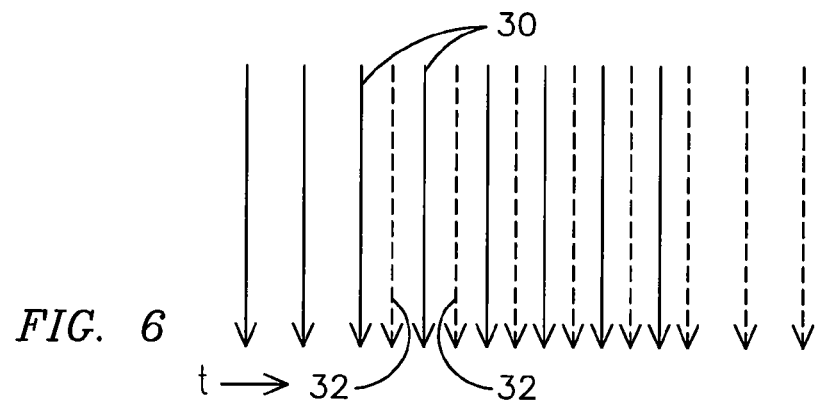
FIG. 6 shows an example scanning sequence for an ultrasound scan according to another embodiment of the invention.

In another example embodiment, a smooth interleaving scheme may be used to reduce motion artifacts compared to group interleaving. As shown in FIG. 6, beams 30 (indicated by continuous lined arrows) of a first frame may be interleaved with beams 32 (indicated by dashed lined arrows) of a second frame so that at least some beams of each of the first and second frames are scanned during a frame interval 24. Interleaving in this manner may be accomplished by interspersing beams 30 from the first frame between beams 32 of the second frame.

Figure 8:
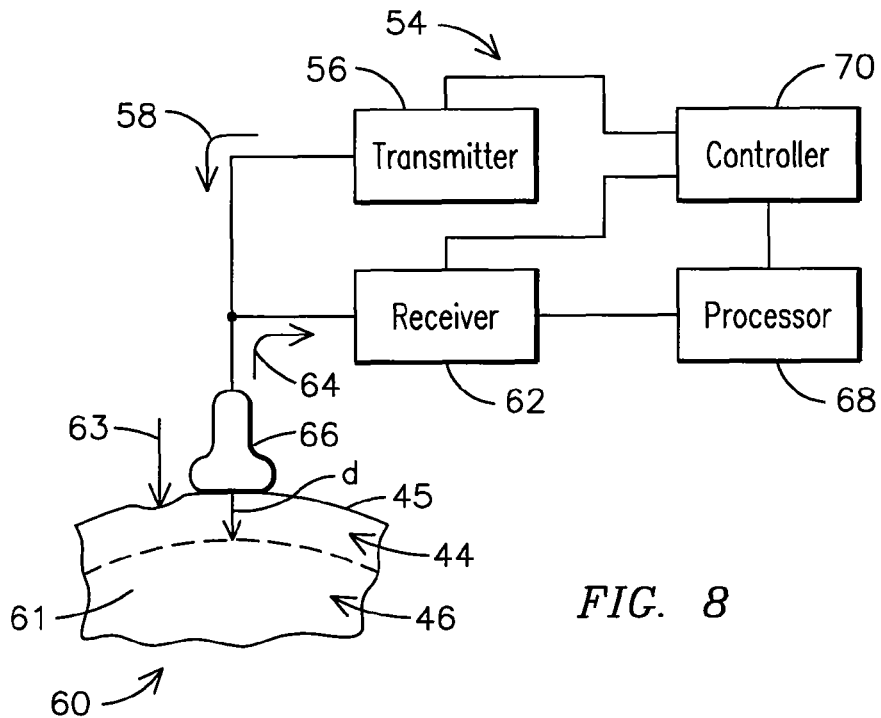
FIG. 8 shows a schematic diagram of an example system for performing a scanning sequence for an ultrasound elasticity scan according to an embodiment of the invention.

In another aspect of the invention, processing the acquired plurality of ultrasound beam echoes to determine a strain variation of the tissue undergoing strain may be based on a distance of the tissue from an ultrasound source. For example, as shown in FIG. 8, a distance (d) may include a depth of the tissue 61 from an ultrasound probe 66 applied to a surface 45 of a subject 60 undergoing an ultrasound elasticity scan. An amount of deformation required for strain estimation may be different for tissue that is relatively close to the probe 66, such as less than about 2 centimeters (cm) (i.e., in a near field) compared to tissue that is relatively far from the probe 66, such as more than about 2 cm (i.e., in a far field) Ultrasound echoes from far field tissue may be more likely to be de-correlated, because the propagation path through the deformed tissue is much longer than for ultrasound echoes signals from near field tissue. Consequently, the strain may have a different quality if the same frame interval is used for signals at the near field and the far field.

Accordingly, a desired scanning value may be determined based on a tissue depth. An expected strain and/or displacement value may be assigned to different depth regions, such as near field and far field regions. The frame interval for desired strain/displacement for each region may be independently estimated based on its assigned strain or displacement value. In addition, in some elasticity imaging situations, such as when using manual compression scanning, optimal strain/displacement for different tissue depths may occur at different times. Rather than wait until an average strain and/or displacement occurs, images at each depth may be updated independently to achieve a faster frame rate perception. Consequently, different pulse repetition intervals between beams of different frames may be used depending of tissue depth. For example, beam echoes may be processed at a longer pulse repetition interval of the beams for tissue being imaged at a shallower depth than tissue being imaged at a deeper depth. Conversely, beam echoes may be processed at a shorter pulse repetition interval for tissue being imaged at a deeper depth than tissue being imaged at a shallower depth.

Figure 7:
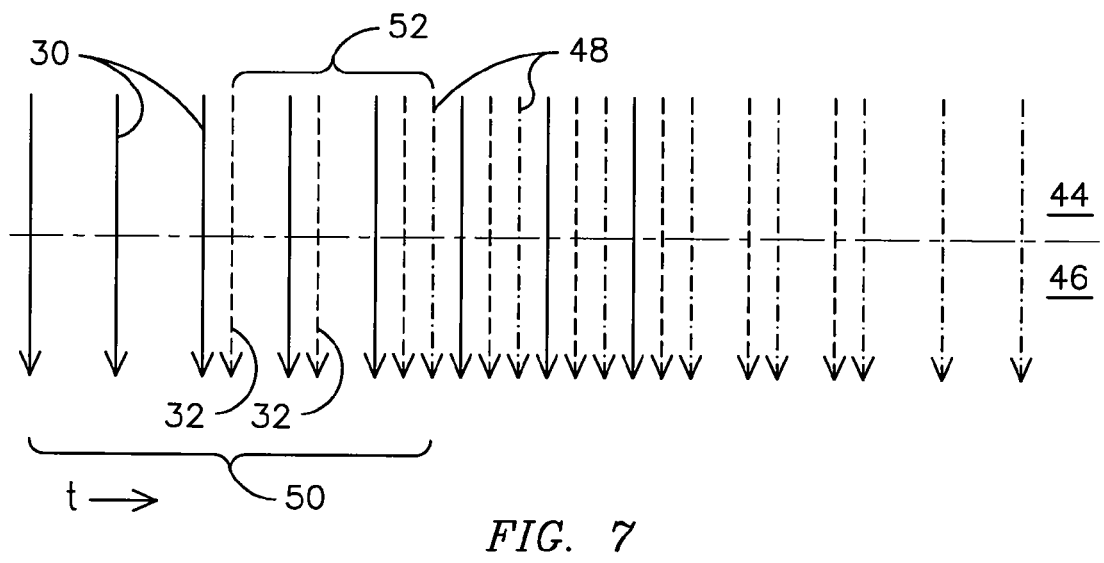
FIG. 7 shows an example scanning sequence for an ultrasound elasticity scan for different tissues depths according to an embodiment of the invention.

FIG. 7 shows example beam scanning sequences that may be used to perform a strain variation estimation based on depth of the tissue. As shown in FIG. 7, strain in the near field 44 may be obtained by comparing beam echoes from solid lined beams 30 with beam echoes from dashed dotted line beams 48 at a pulse repetition interval 50 of fourteen, for example. Strain in the far field 46 may be obtained by comparing beam echoes from dash lined beams 32 with beam echoes from dashed dotted line beams 48 at a pulse repetition interval 52 of seven, for example. Accordingly, far field strain estimation may be obtained more quickly than near field estimation.

FIG. 8 shows a system 54 for performing a scanning sequence for an ultrasound scan, such as one or more of the example scanning sequences described above. The system 54 may include a transmitter 56 for transmitting ultrasound beams 58 to tissue 61 of a subject 60 during an ultrasound scan. The system 54 may also include a receiver 62 for receiving beam echoes 64 from the subject 60 responsive to the transmitted ultrasound beams 58. An ultrasound probe 66 may be configured for receiving the ultrasound beams 58 from the transmitter 56 and providing beam echoes 64 from the subject 60 to the receiver 62.

The system 54 may also include a processor 68 for processing a plurality of the echoes signals 64 to determine a strain variation of the tissue 61 undergoing strain as a result of force 63, for example, calculating a value for an ultrasound scanning frame interval adapted for imaging the tissue 61 undergoing the determined strain variation, and setting the value of the ultrasound scanning frame interval for acquiring ultrasound elasticity images of the tissue 61 undergoing the determined strain variation. The system may also include a controller 70 in communication with the processor 68 for controlling an operation of the transmitter according to the value of the ultrasound scanning frame. The controller 70 may be in communication with the transmitter 56 for controlling the transmitter 56 to transmit beams according to a desired frame interval and/or beam scanning sequence. The controller 70 may also be in communication with the receiver 62 to process received beam echoes 64 according to the frame interval and/or scanning sequence.

Figure 9:
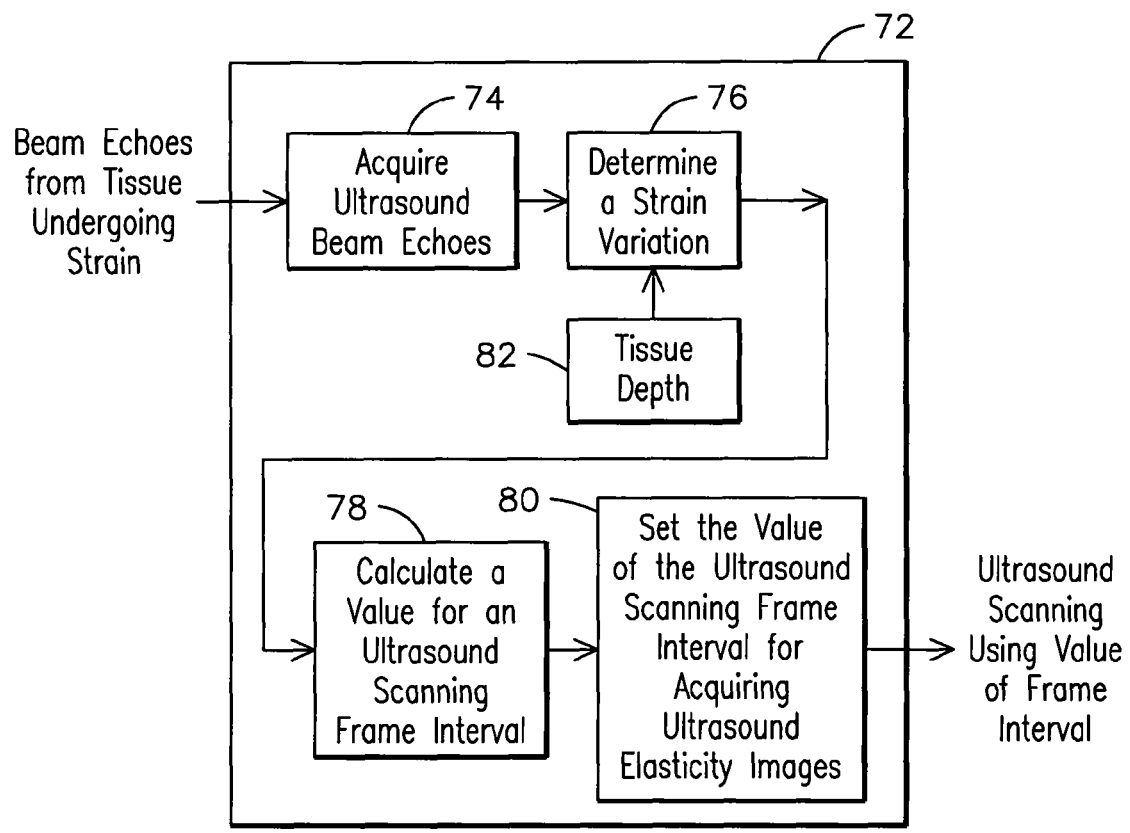
FIG. 9 shows a schematic diagram of an example apparatus for performing a scanning sequence for an ultrasound elasticity scan according to an embodiment of the invention.

FIG. 9 shows an example apparatus 72 for adaptively controlling a frame interval between ultrasound scanning frames of an ultrasound elasticity imaging scan is shown. The apparatus may include a first module 74 for acquiring a plurality of ultrasound beam echoes from tissue undergoing strain and a second module 76 processing the acquired plurality of ultrasound beam echoes to determine a strain variation of the tissue undergoing strain. The apparatus may also include a third module 78 for calculating a value for an ultrasound scanning frame interval adapted for imaging the tissue undergoing the determined strain variation and a fourth module 80 for setting the value of the ultrasound scanning frame interval for acquiring ultrasound elasticity images of the tissue undergoing the determined strain variation. The value of the frame interval may then be used for performing an ultrasound scan to achieve improved ultrasound elasticity imaging results. The apparatus 72 may also include a fifth module 82 for providing tissue depth information to the second module 76 to be used for processing the acquired plurality of ultrasound beam echoes.

Based on the foregoing specification, the invention may be implemented using computer programming or engineering techniques including computer software, firmware, hardware or any combination or subset thereof, wherein the technical effect is to adaptively control a frame interval between ultrasound scanning frames of an ultrasound elasticity imaging scan. Any such resulting program, having computer-readable code means, may be embodied or provided within one or more computer-readable media, thereby making a computer program product, i.e., an article of manufacture, according to the invention. The computer readable media may be, for instance, a fixed (hard) drive, diskette, optical disk, magnetic tape, semiconductor memory such as read-only memory (ROM), etc., or any transmitting/receiving medium such as the Internet or other communication network or link. The article of manufacture containing the computer code may be made and/or used by executing the code directly from one medium, by copying the code from one medium to another medium, or by transmitting the code over a network.

One skilled in the art of computer science will easily be able to combine the software created as described with appropriate general purpose or special purpose computer hardware, such as a microprocessor, to create a computer system or computer sub-system embodying the method of the invention. An apparatus for making, using or selling the invention may be one or more processing systems including, but not limited to, a central processing unit (CPU), memory, storage devices, communication links and devices, servers, I/O devices, or any sub-components of one or more processing systems, including software, firmware, hardware or any combination or subset thereof, which embody the invention.

While certain embodiments of the present invention have been shown and described herein, such embodiments are provided by way of example only. Numerous variations, changes and substitutions will occur to those of skill in the art without departing from the invention herein. Accordingly, it is intended that the invention be limited only by the spirit and scope of the appended claims.

What is claimed is:

1. A method comprising:
   directing a plurality of first detective ultrasound beams into the tissue undergoing strain at a first pulse repetition interval, the first detective ultrasound beams directed into the tissue such that the first detective ultrasound beams are equally spaced within a region of interest in the tissue;
   acquiring a plurality of detective ultrasound beam echoes from tissue undergoing strain from an external force, wherein the plurality of detective ultrasound echoes are echoes of the plurality of first detective ultrasound beams;
   calculating a strain variation of the tissue undergoing strain by processing the plurality of detective ultrasound beam echoes that is acquired;
   determining a period and a phase of the strain variation of the tissue responsive to the external force being applied using a vibrational device;
   calculating a value for an ultrasound scanning frame interval adapted for imaging the tissue undergoing strain based on the strain variation that is calculated, wherein the value of the ultrasound scanning frame interval is calculated based on how an external force is applied to the tissue undergoing strain, the value of the ultrasound scanning frame interval being calculated as an average strain variation responsive to the external force being applied using free hand palpation while the value of the ultrasound scanning frame interval is calculated from a history of previously calculated average strain variations responsive to the external force being applied using a vibrational device;
   setting the value of the ultrasound scanning frame interval for acquiring an ultrasound elasticity image of the tissue undergoing strain;
   responsive to the value of the ultrasound scanning frame interval being less than a predetermined length of an ultrasound scanning frame of an ultrasound elasticity imaging scan, interleaving detective ultrasound beams of a first frame with imaging ultrasound beams of a second frame so that one or more detective ultrasound beams and one or more imaging ultrasound beams of each of the first and second frames are scanned during the frame interval;
   wherein the imaging ultrasound beams are directed into the tissue undergoing strain at a second pulse repetition interval that differs from the first pulse repetition interval;
   acquiring a plurality of imaging ultrasound beam echoes of the plurality of imaging ultrasound beams, wherein the value of the ultrasound scanning frame interval is set such that acquiring the plurality of imaging ultrasound beams echoes is synchronized with the period of the strain variation; and
   generating an image of the tissue based on the plurality of imaging ultrasound beam echoes.

2. The method of claim 1, further comprising generating two or more images of the tissue undergoing strain.

3. The method of claim 1, further comprising reducing a number of the imaging ultrasound beams transmitted into the tissue undergoing strain responsive to setting the value of the ultrasound scanning frame interval and imaging the tissue undergoing strain based on the plurality of imaging ultrasound beam echoes of the imaging ultrasound beams.

4. The method of claim 3, further comprising directing the imaging ultrasound beams into the tissue undergoing strain at a predetermined time interval.

5. The method of claim 4, wherein calculating the value is performed based on at least one of the predetermined time interval or a designated strain variation.

6. The method of claim 1, further comprising, responsive to the value of the ultrasound scanning frame interval being less than a predetermined length of an ultrasound scanning frame of an ultrasound elasticity imaging scan:

truncating at least one of the imaging ultrasound beams in at least one of plural frames; and concatenating the plural frames so that one or more of the imaging ultrasound beams of each of the plural frames are scanned during the ultrasound scanning frame interval.

7. The method of claim 1, wherein interleaving the detective ultrasound beams with the imaging ultrasound beams comprises:

grouping the one or more detective ultrasound beams from the first frame into a first beam group;

grouping the one or more imaging ultrasound beams from the second frame into a second beam group; and interspersing the one or more detective ultrasound beams in the first beam group of the first frame between the one or more imaging ultrasound beams in the second beam group of the second frame.

8. The method of claim 1, wherein interleaving the detective ultrasound beams with the imaging ultrasound beams comprises interspersing the detective ultrasound beams from the first frame between the imaging ultrasound beams of the second frame.

9. The method of claim 1, further comprising:

positioning a source of the detective ultrasound beams and the imaging ultrasound beams proximate a subject for performing an ultrasound elasticity imaging scan of the tissue undergoing strain; and processing the plurality of detective ultrasound beam echoes based on a distance of the tissue undergoing strain from the source of the detective ultrasound beams and the imaging ultrasound beams.

10. A method comprising:

positioning a source of ultrasound beams proximate a subject for performing an ultrasound elasticity imaging scan of tissue undergoing strain from an external force;

directing a plurality of detective ultrasound beams into the tissue undergoing strain at a first pulse repetition interval, the detective ultrasound beams directed into the tissue such that the detective ultrasound beams are equally spaced within a region of interest in the tissue;

acquiring a plurality of ultrasound beam echoes from the tissue, wherein the plurality of detective ultrasound echoes are echoes of the plurality of detective ultrasound beams;

calculating a strain variation of the tissue undergoing strain based on a distance of the tissue from the source based on the plurality of ultrasound beam echoes, wherein the strain variation is calculated by calculating strains of the tissue as a function of depth into the tissue and determining an average of the strains along the depth as the strain variation;

calculating a value for an ultrasound scanning frame interval adapted for imaging the tissue undergoing strain based on the strain variation that is calculated; and setting the value of the ultrasound scanning frame interval for acquiring one or more ultrasound elasticity images of the tissue undergoing strain;

responsive to the value of the ultrasound scanning frame interval being less than a predetermined length of an ultrasound scanning frame of an ultrasound elasticity imaging scan, interleaving detective ultrasound beams of a first frame with imaging ultrasound beams of a second frame so that one or more detective ultrasound beams and one or more imaging ultrasound beams of each of the first and second frames are scanned during the frame interval;

wherein the imaging ultrasound beams are directed into the tissue undergoing strain at a second pulse repetition interval that differs from the first pulse repetition interval;

acquiring a plurality of imaging ultrasound beam echoes of the plurality of imaging ultrasound beams, wherein the value of the ultrasound scanning frame interval is set such that acquiring the plurality of imaging ultrasound beams echoes is synchronized with the period of the strain variation; and generating an image of the tissue based on the plurality of imaging ultrasound beam echoes.

11. The method of claim 10, wherein the plurality of ultrasound beam echoes is processed at a longer pulse repetition interval for tissue being imaged at a shallower depth than tissue being imaged at a deeper depth.

12. The method of claim 10, wherein the plurality of ultrasound beam echoes is processed at a shorter pulse repetition interval for tissue being imaged at a deeper depth than tissue being imaged at a shallower depth.

13. The method of claim 10, wherein the plurality of ultrasound beam echoes is processed at a pulse repetition interval that is based on a depth at which for tissue being imaged at a deeper depth than tissue being imaged at a shallower depth.

14. A method comprising:

directing a plurality of first detective ultrasound beams into tissue undergoing strain from an external force at a first pulse repetition interval, the first detective ultrasound beams directed into the tissue such that the first detective ultrasound beams are equally spaced within a region of interest in the tissue;

receiving one or more first ultrasound echoes of one or more first ultrasound beams off of a tissue undergoing strain;

determining a strain variation of the tissue undergoing strain based on the one or more first ultrasound echoes;

determining a period and a phase of the strain variation of the tissue responsive to the external force being applied using a vibrational device;

calculating a frame interval for one or more second ultrasound beams based on the strain variation;

responsive to the value of the ultrasound scanning frame interval being less than a predetermined length of an ultrasound scanning frame of an ultrasound elasticity imaging scan, interleaving detective ultrasound beams of a first frame with imaging ultrasound beams of a second frame so that one or more detective ultrasound beams and one or more imaging ultrasound beams of each of the first and second frames are scanned during the frame interval;

wherein the imaging ultrasound beams are directed into the tissue undergoing strain at a second pulse repetition interval that differs from the first pulse repetition interval;

acquiring a plurality of imaging ultrasound beam echoes of the plurality of imaging ultrasound beams, wherein the value of the ultrasound scanning frame interval is set such that acquiring the plurality of imaging ultrasound beams echoes is synchronized with the period of the strain variation; and generating an image of the tissue based on the plurality of imaging ultrasound beam echoes; and modifying a scanning sequence of the one or more second ultrasound beams responsive to the frame interval that is calculated being less than an ultrasound scanning frame.

15. The method of claim 14, wherein the frame interval is calculated based on a depth of the tissue being imaged by the one or more second ultrasound beams.

\* \* \* \* \*